(12) United States Patent
Lee et al.

(10) Patent No.: US 6,274,308 B1
(45) Date of Patent: Aug. 14, 2001

(54) METHOD FOR PURIFYING NUCLEIC ACIDS

(75) Inventors: Dong-Hun Lee, Hackensack, NJ (US); Alfred M. Prince, Pound Ridge, NY (US)

(73) Assignee: New York Blood Center, Inc., New York, NY (US)

( * ) Notice: Subject to any disclaimer, the term of this patent is extended or adjusted under 35 U.S.C. 154(b) by 0 days.

(21) Appl. No.: 09/268,975

(22) Filed: Mar. 16, 1999

Related U.S. Application Data

(63) Continuation-in-part of application No. 08/900,907, filed on Jul. 28, 1997, now Pat. No. 5,958,677.

(51) Int. Cl.$^7$ ................................ C12Q 1/70; C12Q 1/68

(52) U.S. Cl. ....................................... 435/5; 435/6

(58) Field of Search ........................................ 435/6, 91.2

(56) References Cited

U.S. PATENT DOCUMENTS

| | | | |
|---|---|---|---|
| 5,124,041 | 6/1992 | Sheer et al. | 210/641 |
| 5,151,189 | 9/1992 | Hu et al. | 210/635 |
| 5,187,083 | 2/1993 | Mullis | 435/91.2 |
| 5,234,824 | 8/1993 | Mullis | 435/91.2 |
| 5,336,596 | * 8/1994 | Bronstein et al. | 435/6 |
| 5,340,449 | * 8/1994 | Shukla | 204/180.1 |
| 5,438,128 | * 8/1995 | Nieuwkerk et al. | 536/25.4 |
| 5,447,864 | * 9/1995 | Raybuck et al. | 435/270 |
| 5,552,325 | 9/1996 | Nochumson et al. | 436/177 |

OTHER PUBLICATIONS

Porter et al, Nucleic Acid Res 19: 4011 1991.*

Ali N, and Jameel S, "Direct Detection of Hepatitis C Virus RNA in Serum by Reverse Transcription PCR," *BioTechniques* 15(1):40–41 (1993).

Boom R, Sol CJA, Salimans MMM, Jansen CL, Wertheim–VanDillen PME, and Noordaa J, "Rapid and Simple Method for Purification of Nucleic Acids," *Journal of Clinical Microbiology*, 28(3):495–503 (1990).

Cheung RC, Matsui SM, and Greenberg HB, "Rapid and Sensitive Method for Detection of Hepatitis C Virus RNA by Using Silica Particles," *Journal of Clinical Microbiology*, 32(10):2593–2597 (1994).

Chirgwin JM, Przybyla AE, MacDonald RJ, and Rutter WJ, "Isolation of Biologically Active Ribonucleic Acid from Sources Enriched in Ribonuclease," *Biochemistry*, 5294–5299 (1979).

Chomczynski P, "A Reagent for the Single–Step Simultaneous Isolation of RNA, DNA and Proteins from Cell and Tissue Samples," *BioTechniques*, 15(3):532–536 (1993).

Chomczynski P, and Sacchi N, "Single–Step Method of RNA Isolatin by Acid Guanidinium Thiocyanate–Phenol–Chloroform Extraction," *Analytical Biochemistry* 162:156–159 (1987).

Gretch D, Lee W. and Corey L, "Use of Aminotransferase, Hepatitis C Antibody, and Hepatitis C Polymerase Chain Reaction RNA Assays to Establish the Diagnosis of Hepatitis C Virus Infection in a Diagnostic Virology Laboratory," *Journal of Clinical Microbiology*, 30(8):2145–2149 (1992).

Hayashi Y, Kaneko S, Jomori T, Kobara Y, Suzuki E, Tasaka F, Murakami S, Kobayashi K, and Mitani T., "A Simple single–tube procedure of PCR assay for the detection of hepatitis C virus RNA," *Res. Virol.* 145:123–128 (1994).*

Inchauspe G, Zebedee S, Lee D, Sugitani M, Nasoff M, and Prince AM, "Genomic Structure of the Human prototype strain H of hepatitis C virus: Comparison with American and Japanese isolates," *Proc. Natl. Acad. Sci. USA* 88:10292–10296 (1991).*

Kaneko S, Feinstone SM, and Miller RH, "Rapid and Sensitive Method for the Detection of Serum Hepatitis B Virus DNA Using the Polymerase Chain Reaction Technique," *Journal of Clinical Microbiology*, 27(9):1930–1933 (1989).*

Lai J, Prince AM, Wolfe L, and Andrus L, "A Simplified Method for PCR Detection of Hepatitis C Virus RNA from Human Serum," *PCR Methods and Applications* 3:308–309 (1994).*

Macfarlane DE, and Dahle CE, "Isolating RNA from whole blood—the dawn of RNA–based diagnosis," *Nature* 362(11):186–188 (1993).*

MicroProbe Corporation "IsoQuick® Nucleic Acid Extraction Kit," Technical Information, (1992).*

"Mini–Price Minipreps on Vacuum Manifolds," *Qiagen News for Biochemistry and Molecular Biology*, Issue No. 1/95.*

Qiagen, *Bio Robot 9600* "QIAwell Ultra Plasmid Kits".*

Qiagen QIAamp Viral RNA Handbook: For purification of viral RNA from plasma, serum and cell–free body fluids, (1996).

Qiagen, "RNeasy 96 Kits for high–throughput total RNA isolation," *Qiagen Technical Service*, (1997).

Qiagen Product Guide 1997.

"QIAmp HCV Kit for Hepatitis C Virus RNA Purification from Plasma," *Qiagen News for Biochemistry and Molecular Biology*, Issue No. 2/95.

Ravaggi A, Primi D, and Cariani E, "Direct PCR Amplificatino of HCV RNA from Human Serum," *PCR Methods and Applications*, 1:291–292 (1992).

(List continued on next page.)

Primary Examiner—Eggerton A. Campbell
(74) Attorney, Agent, or Firm—Hoffmann & Baron, LLP

(57) ABSTRACT

The invention relates to a method for purifying of a nucleic acid from a biological sample. The method involves contacting a biological sample containing a nucleic acid with a hydrophilic polyvinylidene fluoride (PVDF) membrane which contains pores having an average diameter less than about 0.45 µm and recovering the nucleic acid. The method can further include adding silica beads to the biological sample prior to the contacting step.

27 Claims, No Drawings

OTHER PUBLICATIONS

Robertson BH, "PCR Detection and Analysis of Hepatitis Viruses," in Clewley JP ed. The Polymerase Chain Reactin (PCR) for Human Viral Diagnosis, *CRC Press*: 57–80 (1995).

Schenborn ET, and Mierendorf RC, "A novel transcription property of SP6 and T7 RNA polymerases: dependence on template structure," *Nucleic Acids Research*, 13 (17):6223–6236 (1985).

Su S, Vivier RG, Dickson MC, Thomas N, Kendrick MK, Williamson NM, Anson JG, Houston JG, and Craig FF, "High–Throughput RT–PCR Analysis of Multiple Transcripts Using a Microplate RNA Isolation Procedure," *BioTechniques* 22:1107–1113 (1997).

Wang CNJ, Wu KY, and Wang H, "Quantitative PCR Using the AmpliSensor Assay," in Dieffenbach, CW and Dveksler, GS, eds., *PCR Primer: A Laboratory Manual*, Cold Spring Harbor Laboratory Press: 193–202 (1995).

1994–1995 Millipore Direct, "Membranes/Depth Filters/Disc Filters," Technical Information:13–21.

\* cited by examiner

METHOD FOR PURIFYING NUCLEIC ACIDS

This application is a continuation-in-part of application Ser. No. 08/900,907, filed Jul. 28, 1997, now U.S. Pat. No. 5,958,677 on behalf of the same inventors.

BACKGROUND OF THE INVENTION

The present invention relates to methods for purifying nucleic acids from biological samples containing nucleic acids and other materials. More specifically, the invention relates to methods for rapid and automatable purification of viral RNA from cell free biological samples.

Contamination of the blood supply with pathogenic viruses such as human immunodeficiency virus (HIV) and hepatitis has become an increasingly serious problem. The prevailing opinion in the NIH and elsewhere is that within 2–5 years all blood should be screened using polymerase chain reaction (PCR) analysis in addition to serological tests. It is thought that this will prevent at least one hundred transfusion-associated cases of hepatitis B virus (HBV), hepatitis C virus (HCV), and HIV per year. Serological tests were until recently the method of choice for screening blood. Serological tests detect the presence of antibodies raised against viral agents in the blood. These tests, while easy to perform and efficient, have the drawback of not being able to detect an infection if an antibody response is not mounted. It is, therefore, difficult to use the tests to detect individuals in the early stages of infection. Because of this and other practical limitations to serological testing, there is a real need for methods that will detect infection during the window period before the standard serological tests are viable. Isolating viral nucleic acids present in the blood plasma followed by PCR amplification enables the detection of virus at the earliest stages of infection. The detection of virus at these stages is crucial to insure that the blood supply is free from contamination.

The screening of blood and related biological materials in the medical setting is performed on a massive scale. If we include the screening of plasma for the preparation of blood derivatives, around 20 million tests are done per year. Blood centers commonly test as much as one thousand units of blood each day. The preparation of isolated nucleic acids from a thousand samples of blood per day using the presently available techniques would require a huge staff of technicians. There is clearly a great need for rapid automatable methods for the detection of viral RNA during the early stages of infection to safeguard the blood supply against viral contamination.

Purifying viral RNA has been complicated in the past by the need for time-consuming procedures such as organic extractions and precipitation steps. There has long been a need for simple and efficient methods to purify RNA. The standard procedures for the purification of either RNA or DNA involve the solubilization of cells or virions either by the use of chaotropic ions such as guanidinium isothiocyanate (GuSCN) or by the dissolution of proteins by proteinase K. Solubilization is then followed by nucleic acid purification steps such as phenol/chloroform extraction, alcohol precipitation, and washing (Chomczynski et al. 1987). Methods lacking the above-mentioned nucleic acid purification steps have been found to suffer from interference by inhibitors of the enzymes used in PCR that are present in many sera or, in our experience, give false negative results when tested on undiluted samples (Ali et al. 1993; Ravaggi et al. 1992; Lai et al. 1994; Hayashi et al. 1994). Thus, the majority of existing methods are unsuitable for automated PCR because of either the necessity of performing multiple steps or their general unreliability.

One currently available method and kit for the purification of certain viral RNA from plasma uses a silica gel-based membrane (QIAGEN News 1995). However, this method is specifically adapted to purification of the RNA from a single virus, i.e., HCV, and further involves numerous centrifugations and is therefore not amenable to automation. An automated RNA purification system based on the use of silica-gel based membranes is also available (QIAGEN Catalogue 1997).

In view of the above considerations, it is clear that simpler and faster methods of RNA purification are needed. Methods compatible with automation are especially sought after.

Accordingly, it is one of the purposes of this invention to overcome the above limitations in the purification of RNA of viral origin by providing a method that enables the automation of the step of extraction of nucleic acids from serum or plasma. An RNA purification method suitable for automation should have a solubilization step, which dissolves cells and viruses and quantitatively liberates the RNA while inactivating, or at least inhibiting, ribonuclease (RNase). In addition, since centrifugation is difficult to incorporate into automated technology, the method should include a capture step in which the desired nucleic acid can be specifically or non-specifically bound to a solid phase permitting inhibitors to be removed by washing.

SUMMARY OF THE INVENTION

It has now been discovered that these and other objectives can be achieved by the present invention, which provides a method for purifying nucleic acids of viral origin. The method allows for the rapid purification of viral RNA from biological samples and is compatible with automation and nucleic acid amplification techniques such as RT-PCR (reverse transcription-PCR). Although a preferred biological sample is blood plasma or serum, the method is compatible with a variety of biological samples from mammalian, bacterial, yeast and plant sources.

In one embodiment the invention is a method for purifying viral RNA, comprising:
(a) applying a biological sample containing viral RNA to a hydrophilic polyvinylidine fluoride (PVDF) membrane which contains pores having an average diameter less than about 0.45 μm;
(b) passing the biological sample through the PVDF membrane;
(c) washing the membrane to remove impurities while selectively retaining the viral RNA;
(d) suspending the viral RNA using an eluant to provide purified viral RNA; and
(e) recovering the purified viral RNA.

Preferably, the membrane contains pores having an average diameter of from about 0.1 μm to about 0.3 μm, more preferably from about 0.15 μm to about 0.25 μm, and still more preferably, about 0.22 μm. The membrane is also preferably low protein-binding.

The passing step can comprise applying a pressure differential across the membrane, such as applying negative pressure below the membrane, or applying positive pressure above the membrane. Alternatively, the passing step can comprise applying centrifugal force to promote flow of the biological sample across the membrane.

The method can further comprise lysing the biological sample before the applying step.

The method is capable of purifying viral RNA having a length less than about 40,000 nucleotides, and is effective to purify viral RNA having a length less than about 30,000 nucleotides. The viral RNA is preferably single stranded. The method is well suited to purify viral RNA from a virus selected from the group consisting of hepatitis C virus, hepatitis A virus, hepatitis G virus, human immunodeficiency virus, human T-cell leukemia virus I, human T-cell leukemia virus II, and human lymphotropic virus.

The method can further comprise removing cellular components of the biological sample prior to applying the sample to the membrane. For example, if the biological sample is a blood sample, the removing step can comprise removing blood cells from the sample.

Alternatively, if the viral RNA is to be obtained from a cell culture, the removing step can comprise removing the cultured cells from the culture medium, to leave a supernatant substantially free of cells. Removal of cells can be accomplished by centrifugation or by a separate filtration step.

In the method, it is preferred that the biological sample be substantially free of cellular components. Especially preferred biological samples include serum or plasma.

The biological sample can contain whole virus. For example, the whole virus can be selected from the group consisting of hepatitis C virus, hepatitis A virus, hepatitis G virus, human immunodeficiency virus, human T-cell leukemia virus I, human T-cell leukemia virus II, and human lymphotropic virus. Whole virus can be disrupted by lysing according to the method to release the viral RNA desired to be purified.

The method can further comprise amplifying the purified viral RNA to provide amplified viral RNA, and can also further comprise quantitating the amplified viral RNA. For example, the method can comprise amplifying the viral RNA using RT-PCR.

The method can also include identifying the viral nucleic acid by hybridizing with an oligonucleotide probe that uniquely hybridizes with nucleic acid of a selected virus.

In another embodiment, the invention is a method for purifying nucleic acid, comprising:
- (a) applying a biological sample containing nucleic acid to a hydrophilic polyvinylidine fluoride (PVDF) membrane which contains pores having an average diameter less than about 0.45 $\mu$m;
- (b) passing the biological sample through the PVDF membrane;
- (c) washing the membrane to remove impurities while selectively retaining the nucleic acid;
- (d) suspending the nucleic acid using an eluant to provide a purified sample; and
- (e) recovering the purified nucleic acid.

The membrane preferably contains pores having an average diameter of from about 0.1 $\mu$m to about 0.3 $\mu$m, more preferably from about 0.15 $\mu$m to about 0.25 $\mu$m, and still more preferably about 0.22 $\mu$m.

The method can be used to purify nucleic acid having a length less than about 40,000 nucleotides, and is well suited to purifying nucleic acid having a length less than about 30,000 nucleotides.

The nucleic acid capable of purification by the method is preferably RNA, and preferably originates from an RNA virus.

In another embodiment the invention is a method for purifying RNA relative to DNA in a sample, comprising:
- (a) applying a sample containing RNA and DNA to a hydrophilic PVDF membrane that contains pore sizes having an average diameter of less than about 0.45 $\mu$m;
- (b) passing the sample through the membrane to selectively retain the RNA;
- (c) washing the membrane; and
- (d) eluting to recover an eluate sample that has a substantially increased proportion of RNA to DNA.

The method is capable of iteration, and can further comprise repeating steps (a) through (d) using the eluate sample to further purify RNA relative to DNA.

Preferably, the hydrophilic PVDF membrane contains pores having an average diameter of from about 0.1 $\mu$m to about 0.3 $\mu$m, more preferably from about 0.15 $\mu$m to about 0.25 $\mu$m, and still more preferably about 0.22 $\mu$m.

In still another embodiment, the invention is a method for screening blood for viruses, comprising:
- (a) applying a plurality of biological samples containing viral nucleic acid to hydrophilic polyvinylidine fluoride (PVDF) membranes containing pores having an average diameter less than about 0.45 $\mu$m;
- (b) passing the biological samples through the PVDF membranes;
- (c) washing the membranes to remove impurities while selectively retaining the viral nucleic acid for each sample;
- (d) suspending the viral nucleic acid using an eluant to provide purified viral nucleic acid for each sample; and
- (e) recovering the purified viral nucleic acid for each sample.

In particular, the method can further comprise prior to the applying step:
- (i) collecting a plurality of blood samples;
- (ii) removing cellular components from the blood samples to provide a plurality of cell-free samples; and
- (iii) lysing the cell-free samples to provide the biological samples.

The method is well adapted for screening blood samples for infection by RNA viruses, inasmuch as the method purifies viral RNA with high efficiency. Thus the method can be used for screening samples for RNA viruses such as hepatitis C virus, hepatitis A virus, hepatitis G virus, human immunodeficiency virus, human T-cell leukemia virus I, human T-cell leukemia virus II, and human lymphotropic virus.

Also, the method can further comprise identifying the viral nucleic acid for each sample using PCR. The method can also further comprise identifying the viral nucleic acid for each sample by hybridizing with an oligonucleotide probe that uniquely hybridizes with nucleic acid of a selected virus.

In yet another embodiment, the invention is a method for evaluating antiviral drugs, comprising:
- (a) obtaining a blood sample of an animal subjected to antiviral treatment;
- (b) isolating blood plasma or serum from the blood sample;
- (c) lysing the blood plasma or serum to provide a lysed sample;
- (d) passing the lysed sample through a hydrophilic polyvinylidine fluoride (PVDF) membrane that contains pores having an average diameter less than about 0.45 $\mu$m;
- (e) washing the membrane to remove impurities while selectively retaining viral nucleic acid from the lysed sample;
- (f) suspending the viral nucleic acid using an eluant to provide purified viral nucleic acid; and (g) amplifying the purified viral nucleic acid by quantitative PCR to establish the viral concentration in the blood sample.

The method is of use in cases wherein the antiviral treatment is directed to an infection by an RNA virus, and the viral nucleic acid is viral RNA. For example, the RNA virus can be selected from the group consisting of hepatitis C virus, hepatitis A virus, hepatitis G virus, human immunodeficiency virus, human T-cell leukemia virus I, human T-cell leukemia virus II, and human lymphotropic virus.

In another embodiment, the invention is a method for testing antiviral vaccines by administering a vaccine to an animal and challenging the animal with a virus, including:

(a) obtaining a blood sample from the animal;
(b) isolating plasma or serum from the blood sample;
(c) lysing the plasma or serum to provide a lysed sample;
(d) applying the lysed sample to a hydrophilic polyvinylidine fluoride (PVDF) membrane that contains pores having an average diameter of less than about 0.45 $\mu$m;
(e) passing the sample through the PVDF membrane to retain viral nucleic acid;
(f) washing the membrane to remove impurities while selectively retaining viral nucleic acid;
(g) suspending the viral nucleic acid using an eluant to provide purified viral nucleic acid;
(g) recovering the purified viral nucleic acid; and
(h) amplifying the purified viral nucleic acid by quantitative PCR to establish the concentration of virus in the original blood sample.

In particular, the method is suited for use in situations wherein the antiviral treatment is directed to an infection by an RNA virus. For example, the RNA virus can be selected from the group consisting of hepatitis C virus, hepatitis A virus, hepatitis G virus, human immunodeficiency virus, human T-cell leukemia virus I, human T-cell leukemia virus II, and human lymphotropic virus.

A significant advantage of the invention is that it provides a method that achieves a purification of RNA such that the samples prepared are suitable for nucleic acid amplification methodology. This feature of the invention enables the rapid detection and identification of viruses present in samples at extremely low concentration levels and the determination of the concentration of virus present in these samples. The fact that this is achieved in a rapid and reliable way makes this method a particularly useful one for screening large numbers of blood samples.

An advantage of the invention of considerable value is that it is readily compatible with automation. The following features of the invention combine to achieve this compatibility. The method includes a solubilization step that dissolves cells and viruses to quantitatively liberate the RNA while inactivating ribonucleases (RNases). In addition, the method includes a capture step in which the nucleic acid is specifically bound to a solid phase permitting inhibitors to be removed by washing. Together, these attributes of the present invention allow numerous samples to be handled concurrently.

In yet another embodiment, the invention is a method for purifying a nucleic acid, comprising:

(a) contacting a biological sample containing a nucleic acid with a hydrophilic polyvinylidine fluoride (PVDF) membrane which contains pores having an average diameter less than about 0.45 $\mu$m; and
(b) recovering the nucleic acid.

The method can further comprise adding silica beads to the biological sample prior to the contacting step. The silica beads preferably have an average diameter of from about 0.2 microns to about 5.0 microns and even more preferably, from about 2.0 microns to about 5.0 microns. The nucleic acid capable of purification by the method is preferably RNA or DNA. Preferably, the membrane contains pores having an average diameter of from about 0.1 $\mu$m to about 0.3 $\mu$m, more preferably from about 0.15 $\mu$m to about 0.25 $\mu$m, and still more preferably, about 0.22 $\mu$m. The membrane is also preferably low protein-binding.

The method can further comprise applying a pressure differential across the membrane after the contacting step, such as applying negative pressure below the membrane, or applying positive pressure above the membrane. Alternatively, the contacting step can comprise applying centrifical force to promote flow of the biological sample across the membrane.

The method can further comprising a lysing the biological sample before the contacting step. If silica beads are added to the biological sample prior to the contacting step, they are added following the lysing step.

The method is capable of purifying nucleic acids having a length less than about 40,000 nucleotides, and is effective to purify nucleic acids having a length less than about 30,000 nucleotides.

The method can further comprise removing cellular components of the biological sample prior to contacting the biological sample to the membrane. For example, if the biological sample is a blood sample, blood cells are removed from the biological sample after the contacting step and prior to the recovering step. Alternatively, if the nucleic acid is to be obtained from a cell culture, the cultured cells are removed from the culture medium after the contacting step and prior to the recovering step. Removal of cells can be accomplished by centrifugation, centrifugation or by a separate filtration step.

In the method, it is preferred that the biological sample be substantially free of cellular components. Especially preferred biological samples include serum or plasma.

The method can further comprise amplifying the nucleic acid to provide amplified nucleic acids, and can also further comprise quantitating the amplified nucleic acid. For example, the method can comprise amplifying the nucleic acid using RT-PCR.

The method can also include identifying the nucleic acid by hybridizing with an oligonucleotide probe that uniquely hybridizes with the nucleic acid.

A preferred embodiment of the invention includes a solid phase that is a filter that defines or partly defines the bottom of the wells of a multi-well filtration plate. RNA trapped on the filter can then be purified by washing. An even more preferred embodiment includes a vacuum manifold to which the multi-well filtration plate is suitably fitted, such that the filtration steps can be carried out via the application of a differential pressure gradient and thereby allowing for the handling of multiple samples in concert. The method of this invention, in the embodiment containing a vacuum manifold and multi-well plates, is very well suited to the processing of large numbers of samples. The pressing need to screen large numbers of blood samples for viruses that may be present in the early stages of infection, highlights and signalizes the great importance of the advantages provided by the method of the invention.

An additional significant advantage is that the simplicity of the RNA purification method of the invention makes it compatible with routine blood screening work. That the method does not require extensive training in laboratory procedures is also of great value.

These and other advantages of the present invention will be appreciated from the detailed description and examples, which are set forth herein. The detailed description and examples enhance the understanding of the invention, but are not intended to limit the scope of the invention.

BRIEF DESCRIPTION OF THE DRAWINGS

Preferred embodiments of the invention have been chosen for purposes of illustration and description, but are not intended in any way to restrict the scope of the invention. The preferred embodiments of certain aspects of the invention are shown in the accompanying drawings, wherein:

FIG. 1 is an electrophoretogram of a 5% polyacrylamide gel comparing the viral purification of hepatitis A virus (HAV) RNA using the method of the invention to a prior art method for purifying viral RNA.

DETAILED DESCRIPTION OF THE PREFERRED EMBODIMENTS

The present invention is directed to a method for rapidly purfying nucleic acids. Nucleic acids are either RNA (ribonucleic acid) or DNA (deoxyribonucleic acid). The invention is compatible with automation and is highly useful for screening blood samples for contaminating viruses.

The invention makes use of the unexpected finding that porous hydrophilic polyvinylidine fluoride (PVDF) membranes specifically and reversibly bind nucleic acids. These membranes will also be referred to as porous filters and filters. Specifically and reversibly binding refers to the retention of nucleic acid by the membrane under certain defined conditions and the subsequent release of the nucleic acid from the membrane when the conditions are altered in a controlled way. The specific and reversible capture of nucleic acids from fluid samples by these membranes makes them highly useful for the purification of nucleic acid. These membranes, at certain pore sizes, have a remarkable unexpected specificity for RNA binding. This specificity is such that the membranes can be used to distinguish RNA from DNA due to a significantly higher affinity for RNA as compared to DNA.

Biological samples derived from different human body fluids, cell culture supernatants, tissues, cells, and other mammalian, plant, bacterial and yeast sources are suited for treatment according to the method of the invention. In a preferred embodiment, the biological sample can be blood plasma or blood serum. Blood serum is obtained from whole blood by centrifugation to remove cellular components. It is a clear solution that separates out from blood upon clotting, and is substantially free of cellular material. Plasma is obtained in a similar way as blood serum except that an anticoagulant is added to the blood. Centrifugation or filtration can be used to produce cell-free samples.

Biological samples, in the context of this disclosure, include fluids that contain substances found in living systems, including nucleic acids, such as viral nucleic acids, and whole virus (viral particles). Fluids can be, but are not limited to, solutions, suspensions, and emulsions. The skilled artisan will appreciate that purification of nucleic acids from the several kinds of samples may require different types of sample preparation, buffer systems, solutions, and other fluids, so as to optimize the method of the invention in the context of the different physical properties of such materials.

In one embodiment, the method of the invention comprises the steps of (a) lysing a biological sample to liberate viral RNA from whole viruses; (b) passing the lysate through a porous filter to selectively capture the viral RNA on the filter; (c) washing the membrane to remove contaminants such as RNase inhibitors, proteins, and lipids, while selectively retaining the viral RNA; (d) eluting the RNA from the filter using a low salt solution; and (e) recovering the RNA in purified form from the solution. The sample of RNA is at this point purified and thus in condition for further analysis.

By "washing the membrane" we mean that wash solution is passed over the membrane to remove impurities.

By "purified," we mean that the RNA has been at least substantially freed of contaminants such as proteins, lipids, and other components found in blood or other biological samples. Purification, as here defined, is meant to describe the extraction of RNA, or other nucleic acid, from a sample such that the resulting RNA sample is free of contaminants to such an extent that it is compatible with amplification by PCR methodology. Of particular significance, a sample that is purified, in the sense meant here, is one that is not contaminated with inhibitors of the enzymes used in PCR. Such inhibitors are present in blood plasma and serum, and have in the past hampered the use of other RNA purification methods where RT-PCR amplification is desired (see Cheung et al. 1994). We consider the terms "purification," "isolation," and "extraction" to be synonymous with each other in the context of this disclosure.

A variety of viruses are amenable to manipulation according to the method of the present invention. The method is well adapted to the purification of RNA originating in RNA viruses. Such RNA viruses include, for example, picornavirus, callcivirus, togavirus, flavivirus, coronavirus, reovirus, rhabdovirus, filovirus, paramyxovirus, orthomyxovirus, bunyavirus, arenavirus, and retrovirus. Viral RNAs are typically found to be in the size range of from about 3,000 to about 30,000 nucleotides. The method of the invention is well suited for the isolation of RNA in this size range. Viruses that the method is well suited to purify, RNA from hepatitis C virus, hepatitis A virus, hepatitis G virus, human immunodeficiency virus, human T-cell leukemia virus I, human T-cell leukemia virus II, and human lymphotropic virus, which all present significant current health risks.

Alternatively, the method can be used to purify DNA, such as viral DNA from DNA viruses. For example, the method can be used to purify DNA from DNA viruses such as poxvirus, herpesvirus, adenovirus, papovavirus, hepadnavirus and parvovirus.

The invention can be used with nucleic acid amplification systems and, in conjunction with other molecular biological techniques, can be used to identify viruses and determine the concentration of virus in blood samples, thereby providing a methodology that establishes the identity and extent of a patient's viral infection. Quantitative PCR and electrophoresis techniques are examples of molecular biological techniques that are useful for these applications of the method of the invention. The use of reverse transcription polymerase chain reaction (RT-PCR) methodology with the invention can be particularly valuable when screening for RNA viruses. In addition, the method of the invention can be used with RT-PCR methodology to study transcription regulation. The rapid analysis of RNA transcripts should facilitate this type of work.

The method can also be used for the separation of RNA from DNA, since a preferred filter system, a hydrophilic polyvinylidine fluoride (PVDF) membrane containing pores of about 0.2 μm, has been unexpectedly found to have a significantly higher affinity for RNA than for DNA. This remarkable feature of the invention is not found with other standard assays, which are not typically capable of distinguishing between RNA and DNA.

The method of this embodiment includes a step of lysing or solubilizing whole virus particles to release their RNA contents. "Lysis" here means the physical disruption of the virus by conventional methods, using chaotropic ions such as guanidinium isothiocyanate (GuSCN) and detergents. Where blood plasma or serum contains whole "assembled" virus, lysis solution cleaves the envelope of the virus, opening the virus and quantitatively liberating the viral RNA. A preferred lysis solution is 5 M GuSCN, 40 mM Tris-HCl, 20 mM EDTA, and 1% Triton X-100. Because of the presence of 5 M GuSCN, this solution also serves to inactivate ribonuclease (RNase). Other protein denaturants could also serve this purpose. The plasma or serum samples are incubated in the lysis solution before the resultant fluid is applied to the hydrophilic PVDF membrane.

The biological sample, preferably lysed, is contacted with the PVDF membrane. Typically, the sample is permitted to flow or pass across the membrane. Preferably, the flow of the sample is promoted by the application of a force that accelerates the fluid flow in the system. For example, in a preferred embodiment, a pressurizing apparatus can be used to provide the promoting force. Thus, apparatus that provides a negative pressure beneath the membrane or a positive pressure above the membrane can be used to provide the necessary force to cause the fluid to flow through the membrane.

A pressurizing apparatus that provides a pressure differential across the membrane is a preferred means for causing fluid to flow through the filter. One of the advantages of such a system is the facility with which such a system can be adapted to large-scale automation and the rapid handling of samples. A more preferred embodiment uses a vacuum manifold to create a vacuum, or negative pressure, below the filter to cause the fluid to flow through the filter. Alternatively, a positive pressure applied above the filter can also be used to cause the fluid to flow through the filter. For example, positive atmospheric pressures of a gas, e.g., air, or an inert gas such as nitrogen, can be employed. The method of this invention is also compatible with the use of centrifugation or gravity to promote fluid passage or flow through the filter.

The nucleic acid bound to the membrane is then washed to remove proteins, lipids, inhibitors and other contaminants by passing washing buffer over the sample and through the filter. A preferred washing solution is an alcohol solution of 50–70% ethanol that contains from about 50 to about 100 mM NaCl, 10 mM Tris-HCl and 2 mM EDTA. Other salts, buffers, chelating agents, and alcohols would also be acceptable for this step. The washing solution should be passed over the bound nucleic acid at least once, and more preferably at least two times, to assure that the contaminants have been removed.

The nucleic acid is then eluted from the filter by passing a low salt eluting solution through the filter. The preferred eluting solution is either nuclease-free $H_2O$ or nuclease-free 10 mM Tris-HCl and 1 mM EDTA. Preferred eluting solutions have low ionic strength, meaning that the concentration of salts and other ionic compounds is kept to a minimum.

Elevated temperatures, i.e., above ambient or room temperature, have been found to increase the nucleic acid elution process of the method. In particular, eluting the nucleic acid at temperatures of about 80° C. has been found to be significantly more efficient than eluting at room temperature.

The membrane (or filter) used in the method of the invention is a porous hydrophilic polyvinylidine fluoride (PVDF) membrane. In a preferred embodiment, a hydrophilic, low protein-binding PVDF membrane having an average pore size of about 0.45 μm or less is used. In a more preferred embodiment, the membrane has an average pore size of about 0.22 μm. Such membranes are commercially available. For example, a hydrophilic low protein-binding Durapore® membrane furnished by Millipore Corporation (Bedford, Mass.) can be used.

Membranes composed of PVDF are naturally hydrophobic. Chemically modified PVDF membranes that are hydrophilic and low in protein binding have now been found to specifically bind viral RNA. That these PVDF membranes are highly effective in the capture and controlled release of viral RNA was an unexpected and novel finding. Data shown in the examples below demonstrate that these membranes are at least as effective for selectively capturing RNA from viral sources as a commercially available method for purifying viral RNA. Other hydrophilic membranes of similar chemical and physical functionality and pore size are also expected to be effective for the purification of viral RNA according to the method described herein.

A preferred embodiment of the method of the invention includes a multiple well (multi-well) filtration plate fitted into a vacuum manifold. The filtration plates have as their filter components the hydrophilic PVDF membranes of the method of the invention. Filtration plates suitable for use with this embodiment of the invention are commercially available. For example, 96-well filtration plates with hydrophilic PVDF membranes as their filtration (membrane) components are sold by Millipore Corporation (Bedford, Mass.) under the name MultiScreen®-GV. Vacuum manifolds, designed to accommodate multiple-well filtration plates, are commercially available and are used routinely to process multiple samples. For example, a vacuum manifold finished by Millipore can be used. This preferred embodiment of the invention comprises the multiple-well filtration plate situated such that the plate sits on a manifold plate support with a sealing gasket around its edge. This preferred embodiment further comprises a multiple-well collection plate placed below the multiple-well filtration plate and fitted to the vacuum manifold in such position that it can collect fluid samples that are passed through the filter. Multiple-well collection plates are commercially available. For example, a 96-well plate sold by Becton Dickinson and Company (Franklin Lakes, N.J.) under the name Microtest® Tissue Culture Plate can be used. The collection plate preferably has wells that match those of the multiple well filtration plate and is fitted below the filtration plate in such a position as to collect the samples as they are passed through the hydrophilic PVDF filters. These plates, both the filtration plate and the collection plate, fit within the vacuum manifold in interlocking superposition such that a fluid impermeable seal is formed between the two plates. Rectangular spaces at the edges of the platform upon which the collection plate sits provide for the communication of the vacuum to the bottom of the wells of the multi-well filtration plate. The apparatus is sealed from contact with the outside environment by a solid housing and gasket connections between the filtration and collection plates and the housing. A vacuum applied below the manifold plate support holding the collection plate is conveyed through the spaces or openings at the edges of the plate support, but within the sealed confines of the vacuum manifold, to the region below the filter plate. This vacuum causes the flow of fluid through the filter plate such that it can be collected in the collection plate.

Although 96-well filter plates and collection plates are readily available commercially and have been used effectively, there is no inherent limitation of the invention associated with this 96-well format. The 96-well plates are commercially available and in common use, but plates containing more or fewer than 96 wells, with the wells containing larger or smaller volumes, can be prepared and implemented depending upon the needs of the user. Collection plates likewise can be adapted to have more or fewer wells of larger or smaller volumes depending on the needs of the user. Skilled artisans will be able to adapt the method with regard to these particulars to fulfill their own needs.

A preferred embodiment of the invention comprises using 96-well plates to handle many samples at the same time. When such plates are fitted to a vacuum manifold, sample fluid can be passed through all the wells simultaneously. Thus, 96 samples may be processed at the same time. An advantage of the method of the invention is that it is adaptable to automation using laboratory robotics. In a more preferred embodiment of the invention, samples are processed using a robotic liquid handling system in conjunction with a microprocessor-controlled vacuum unit to draw the samples through each of the wells simultaneously. This embodiment enables the method of the invention to routinely handle multiple samples. This capacity for automating the purification of nucleic acid is a valuable advantage of the method of the invention. This will be especially valuable when the method of the invention is used for screening blood because many samples need to be processed rapidly.

Other embodiments of the invention use either centrifugation or gravity to cause the sample to flow through the filter. Multi-well plates can be used with specially designed centrifuge systems using plate rotors to process numerous samples simultaneously.

In a preferred embodiment, the invention is used for the purification and/or detection of RNA viruses in the serum or plasma of samples of blood. Samples of blood serum or plasma, some infected with virus, are added to lysis solution. After incubation, these conditions result in the lysis of whole virus thereby releasing the viral nucleic acid. The lysed samples are then added to the wells of the multi-well plates. This is followed by extensive washing, to remove proteins, lipids, inhibitors, and other contaminants from the filter while the viral RNA remains bound to the filter. The RNA bound to the hydrophilic PVDF membrane is then eluted with the low salt eluting solution or $H_2O$ as described above.

Using the vacuum manifold and automation through the use of laboratory robotics makes the method of this invention compatible with the processing of numerous samples to a degree of purity suitable for nucleic acid amplification and other standard analytical techniques. Nucleic acid amplification systems that make use of PCR methodologies have already been automated. The method of the invention, by providing for the automation of RNA purification, will allow for the automation of the whole process whereby blood samples are screened for viruses. The use of nucleic acid amplification technology in conjunction with the method of the invention enables the user of these methods to screen blood for viruses present at extremely low levels. This is an extraordinary advantage provided by the method of the invention because it is often critical to detect viruses at the earliest stages of infection to allow for aggressive antiviral treatments and to insure that the blood supply is not contaminated. For viruses such as HIV, this type of early detection is crucial.

For a general overview of nucleic acid amplification technology and a description of the application of these techniques for viral diagnosis see, e.g., Dieffenbach et al. (1995) and Clewley (1995).

Alternatively, the purified viral RNA (or other nucleic acid) can be identified by hybridization techniques which employ an oligonucleotide probe that is complementary to, and uniquely hybridizes with, a known nucleic acid sequence. The oligonucleotide probe may be RNA or DNA. The technique of Southern hybridization (Southern blotting) is a particularly well known exemplar of such techniques in which a sample of purified nucleic acid is cleaved with restriction endonuclease, separated by gel electrophoresis, and probed with a specific detectable oligonucleotide probe. Other related methods are known in the art. See Sambrook et al. (1989); Hames et al. (1991); and Keller et al. (1991) for other related methods.

The length of the oligonucleotide probe is not critical, as long as it is capable of hybridizing to the target molecule. The oligonucleotide should contain at least 6 nucleotides, preferably at least 10 nucleotides, and, more preferably, at least 15 nucleotides. There is no upper limit to the length of the oligonucleotide probes. However, longer probes are more difficult to prepare and require longer hybridization times. Therefore, the probe should not be longer than necessary. Normally, the oligonucleotide probe will not contain more than 50 nucleotides, preferably not more than 40 nucleotides, and, more preferably, not more than 30 nucleotides.

Such probes can be detectably labeled in accordance with method known in the art, e.g., radiolabels, enzymes, chromophores, fluorophores, and the like, to reveal specific hybridization. For example, if the genome of a virus is known, the nucleic acid sequence can be used as a template for the preparation of selected oligonucleotide probes to uniquely identify that virus if present in a sample of purified nucleic acid. Failure to hybridize means that the viral nucleic acid is not present in the sample. The use of such probes can be performed in conjunction with amplification, to positively identify the presence or absence of a viral infection in a sample.

The capacity of the method of the invention to obtain highly purified RNA samples is also valuable for use with other molecular biological systems where purified RNA is required. Studies of transcriptional regulation will surely profit from the availability of the method of the invention.

The method of the invention is useful for detection and analysis of viral RNA in the blood from virally infected mammals, e.g., primates such as humans, chimpanzees, etc. The method of the invention, in conjunction with nucleic acid amplification technologies, is also useful for testing antiviral drugs and vaccines. For example, an infected animal is administered an antiviral drug. Blood is sampled from the animal, and blood plasma is prepared by addition of an anticoagulant and centrifugation. Samples of blood plasma are then treated with lysis solution. The lysed samples are then applied to the hydrophilic PVDF filters, washed with the above-mentioned wash solution and eluted with the above-mentioned eluting solution. The sample of purified RNA is then examined using quantitative RT-PCR (reverse transcription-PCR). Samples of blood from animals before and after treatments with antiviral agents or vaccines can be compared, allowing for the rapid assessment of the usefulness of such treatments. That the method of the invention is fast and automatable also allows for following the time course of a viral infection or the response of that infection to antiviral agents over a period of time. Vaccines may be tested by challenging vaccinated animals with virus and monitoring the level of virus present in the blood using the method of the invention.

The method of the invention can also be used for screening lymphocytes for HIV infection. Lymphocytes can be separated from whole blood by conventional density gradient centrifugation. These lymphocytes can be homogenized and lysed before being subjected to the method of the invention. Viral RNA can be detected and identified in such samples. This approach can be of great importance when examining the course of a patient's HIV infection because HIV locates in lymphocytes. Virus not integrated into the host cell nucleic acid can be isolated by the methods of the invention.

In another embodiment of the invention, a container with a hydrophilic PVDF membrane secured inside it is used to isolate nucleic acids. Samples containing nucleic acid are added to the container. Sample fluid is removed while the hydrophilic PVDF retains the nucleic acid. The inside of the container is then washed with wash solution and the nucleic acid is then eluted using eluting solution, to provide purified nucleic acid. A preferred sample for this embodiment contains RNA.

Another embodiment of the method of the invention uses a retrieval probe with attached hydrophilic PVDF. The retrieval probe with attached hydrophilic PVDF is placed into a fluid containing nucleic acid. After some stirring the retrieval probe is removed from the fluid and transferred to wash solution. After washing to remove adherent impurities, the retrieval probe is transferred to a solution containing eluting solution and the nucleic acid is then released from the PVDF to provide a purified nucleic acid sample.

A preferred embodiment of the invention comprises contacting a biological sample containing a nucleic acid with hydrophilic polyvinylidine fluoride (PVDF) membrane which contains pores having an average diameter of less than about 0.45 $\mu$m and recovering the nucleic acid. It is further preferred that silica beads are added to the biological sample prior to contacting the biological sample with the PVDF membrane. It is preferable that silica beads used with the invention have an average diameter of from about 0.2 microns to about 5.0 microns and even more preferably from about 2.0 microns to about 5.0 microns. Silica beads particularly suitable for use with the invention are available from Bangs Laboratories (Carmel, Ind.) as Product No. 50004000PN. This embodiment can further comprise lysing the biological sample before the contacting step and further adding silica beads to the biological sample after the lysing step and prior to the contacting step.

The following examples are provided to assist in a further understanding of the invention. The particular materials and conditions employed are intended to be further illustrative of the invention and are not intended to be limiting upon the reasonable scope thereof.

EXAMPLE 1

Binding of RNA by Hydrophilic PVDF

This example demonstrates the finding that hydrophilic PVDF membranes having average pore size of about 0.22 $\mu$m are effective at binding viral RNA. This experiment was originally done with the aim of ascertaining how much silica would be necessary to effectively purify viral RNA. It was unexpectedly found that hydrophilic PVDF membranes bind RNA in a highly specific manner.

HCV (hepatitis C virus) RNA was extracted from human blood plasma. Blood plasma was prepared by centrifuging a sample of HCV-infected blood in the presence of anticoagulation agents. Samples were then subjected to the method of the invention in the presence of varying amounts of silica beads.

Aliquots of 150 $\mu$L of each sample were transferred to a microfuge tube, then 560 $\mu$L of a lysis solution (5 M GuSCN, 40 mM Tris-HCl, 20 mM EDTA and 1% Triton X-100) was added. The samples were vortexed and then incubated for 10 minutes at room temperature. After incubation, 560 $\mu$L of ethanol was added to each sample. The samples were then transferred to the wells of a 96-well filtration plate with wells having bottoms defined by hydrophilic PVDF membranes that contain pores of about 0.22 $\mu$m diameter. Different amounts of silica beads were added to the wells. The 0.22 $\mu$m hydrophilic, low protein-binding Durapore® Membranes furnished by Millipore in a 96-well format under the name MultiScreen®-GV were used (Millipore Corporation, Bedford, Mass.). The plates were fitted to a vacuum manifold, and a vacuum was used to cause the solution to flow through the membranes in all these steps. The samples were then washed twice with 300 $\mu$L of wash solution (75 mM NaCl, 10 mM Tris-HCl, 2 mM EDTA in 50% ethanol). The bound RNA was then eluted with 50 $\mu$L of a hot (80° C.), nuclease free, eluting solution (10 mM Tris-HCl and 1 mM EDTA). (Hot nuclease-free $H_2O$ may also be used as an eluant fluid in this step). The use of only 50 $\mu$L of eluting solution for the elution step results in a relatively concentrated sample of purified RNA. The samples were collected in this elution step in a 96-well plate containing sample collection wells. The purified RNA was then subjected to further analysis.

Quantitative PCR was done using the AmpliSensor® assay system (Biotronics Technologies Corp., Lowell, Mass.). The AmpliSensor® assay system monitors the amplification efficiency of the PCR reaction via a fluorescence resonance energy transfer (FRET)-based detection scheme. Briefly, cDNA products from the HCV RNA were obtained. Then, the products were amplified in an asymmetric manner to generate 200- to 300-nucleotide long single strand target DNA. These single strand products were re-amplified in a semi-nested manner with a fluorescent primer duplex to yield 50–100 bp amplicons. These were then quantitated on the AmpliSensor® Minilyzer (Biotronics). The quantitation of the different samples studied was based on the relative amount of RNA when compared to a dilution series from a known quantity of synthetic RNA molecules (see Wang et al. 1995). PCR primers were supplied with the AmpliSensor® kit.

The RNA samples were first reverse transcribed. The reverse transcription reaction was carried out in 20 $\mu$L sample volumes with 50 mM Tris-HCl (pH 8.9), 75 MM KCl, 10 mM DTT, 1.5 mM $MgCl_2$, 0.2 mM of each dNTP, 0.12 $\mu$M RT primer, 12U RNase Inhibitor RNasin (Promega, Madison, Wis.) and 20U M-MLV reverse transcriptase (Gibco BRL, Gaithersburg, Md.). The reaction was carried out at 42° C. for 45 min, 90° C. for 2 min, and 25° C. for 20 sec, using an AG 9600 Cycler (Biotronics). After reverse transcription, these samples were then asymmetrically amplified.

The reverse transcribed RNA samples were then subjected to asymmetric amplification according to the following protocol. A 24 $\mu$L sample containing 1U of Taq polymerase (Promega, Madison, Wis.), and a final concentration of 50 mM Tris-HCl (pH 8.7), 40 mM KCl, 1 mM DTT, 0.5 mM of each DNTP, 4 mM $MgCl_2$, 0.12 $\mu$M Limiting primer, and 0.9 $\mu$M Excess primer was prepared. A 25-cycle amplification was run at 95° C. for 20 sec, 60° C. for 30 sec, and 72° C. for 45 sec, using the AG 9600 Cycler (Biotronics). This PCR product mixture was then subjected to semi-nested amplification and detection.

Semi-nested amplification and detection was carried out as follows: 4 $\mu$L AmpliSensor® primer duplex (1.5 ng/$\mu$L) (Biotronics) was added to the above PCR product mixture. An amplification cycle was run at 95° C. for 20 sec, 60° C. for 30 sec, and 72° C. for 30 sec. using the AG 9600 Cycler (Biotronics). A fluorescent readout system, AmpliSensor® Minilyzer (Biotronics) was used for detection. A base reading was established after one amplification cycle. Thereafter, assay readings were carried out at every third cycle.

Raw data were analyzed using the AmpliSensor® analysis program (Biotronics), which establishes a linear standard curve with standards to quantitate unknown samples of RNA.

The results are shown in Table 1.

TABLE 1

HCV RNA Recovery with Varying Amounts of 4 $\mu$m Silica Beads

| Dilution | Bead Amount | | | |
|---|---|---|---|---|
| ($10^X$) | 0 mg | 0.025 mg | 0.25 mg | 2.5 mg |
| | Virus Quantity in log (molecules/mL) | | | |
| HCV RNA −1 | 6.60 | 6.45 | 6.48 | 6.32 |
| −2 | 5.75 | 5.46 | 5.54 | 5.29 |
| −3 | 4.97 | 4.36 | 4.79 | 4.37 |
| −4 | 3.64 | 3.74 | 3.68 | 3.57 |

Table 1 shows the RNA recovery for the method of the invention in the presence of different quantities of silica beads. It was expected that the silica beads, which are commonly used to retain RNA for purification, would bind RNA. The hydrophilic PVDF filters were present only for convenience as part of the filter plates used. Unexpectedly, we discovered that hydrophilic PVDF bound RNA and that the silica beads could not improve on this RNA binding. The prior art indicated that silica would be useful for purifying RNA and, unexpectedly, we found hydrophilic PVDF accomplishes this with a high degree of specificity.

EXAMPLE 2

Quantitative PCR Comparison of the Method of the Invention with Prior Art Method of Viral RNA Purification This example demonstrates that the RNA purification method of the invention gives results that are at least as efficient as those obtained using a commercially available kit for purification of hepatitis C virus RNA from plasma. Viral nucleic acid was extracted with the method of the invention or the QIAamp HCV kit sold by QIAGEN Inc. (Chatsworth, Calif.). The results of the two purification methods are compared for a variety of samples using quantitative PCR or polyacrylamide gel electrophoresis. The following samples were used:

(1) HCV (hepatitis C virus) RNA: RNA was extracted from human blood plasma. Blood plasma was prepared by centrifuging a sample of HCV-infected blood in the presence of anticoagulation agents.

(2) HIV (human immunodeficiency virus) RNA: Human peripheral blood lymphocytes (PBL) were grown in the presence of phytohemagglutini (PHA), a cell growth stimulant, washed, and infected with HIV. After two weeks of culture, cells were harvested and centrifuged. The cell free supernatant containing virus was then collected. HIV RNA was extracted from the supernatant.

(3) HIV DNA: A 12 KB plasmid containing HIV-I (BH10 strain) was added to normal human serum and then extracted.

(4) HBV (hepatitis B virus) DNA: Blood from an HBV-infected chimpanzee was centrifuged and the serum was removed. The DNA was then extracted from the serum.

(5) HAV (hepatitis A virus): HAV RNA was extracted from the supernatant of HAV infected BSCL (African green monkey kidney cells) cells. Cells were harvested and centrifuged. The supernatant was removed, and RNA was extracted from the supernatant.

Samples were subjected to lysis by transferring an aliquot of 150 $\mu$L of sample to a microfuge tube, then adding 560 $\mu$L of a lysis solution (5 M GuSCN, 40 mM Tris-HCl, 20 mM EDTA and 1% Triton X-100). The samples were vortexed and then incubated for 10 min at room temperature. After incubation, 560 $\mu$L of ethanol was added to each sample. The samples were then applied to the filters of a 96-well filtration plate (MultiScreen®-GV, Millipore) with the bottoms of the wells defined by hydrophilic PVDF membranes containing pores with an average diameter of about 0.22 $\mu$m. The plates were fitted to a vacuum manifold, and a vacuum was used to cause the solution to flow through the membranes in all these steps. The vacuum manifold was also purchased from Millipore.

The samples were then washed twice with 300 $\mu$L of a wash solution (75 mM NaCl, 10 mM Tris-HCl, 2 mM EDTA in 50% ethanol). The bound nucleic acid was then eluted with 50 $\mu$L of a hot (80° C.), nuclease-free, eluting solution (10 mM Tris-HCl and 1 mM EDTA). The use of only 50 $\mu$L of solution for the elution step results in a relatively concentrated sample of purified nucleic acid. The samples, when the method of the invention was used, were then collected in a 96-well plate containing sample collection wells. The purified nucleic acid was then subjected to further analysis.

The nucleic acid from these samples was also purified by the prior art method according to the manufacturer's instructions (QIAGEN News 1995). This method uses a silica-gel based column.

The use of a vacuum manifold setup in these experiments demonstrates the invention's adaptability to automation using laboratory robotics. Robotics enables the user of the method to simultaneously deliver all the samples to the wells of the plate such that a plurality of samples can be handled at one time. Laboratory robotics is now in common use in laboratories.

The samples prepared using the 96-well filtration plates involved multiple transfers to the wells because the 300 $\mu$L capacity of these wells was not large enough to contain the whole volume of the samples. Large well volumes can be used to solve this problem. For example, wells with capacities of several milliliters would be useful.

Quantitative PCR for HIV RNA, HCV RNA, HIV DNA, and HBV DNA was done using the AmpliSensor® assay system (Biotronics) generally as described in Example 1. The quantitation of the different samples studied was based on the relative amount of RNA/DNA when compared to a dilution series from a known quantity of synthetic RNA/DNA molecules (see Wang et al. 1995).

The RNA samples were first reverse transcribed in general accordance with Example 1. The reverse transcribed RNA samples and DNA samples were then subjected to asymmetric amplification according to the following protocol. A 24 μL sample containing 1U of Taq polymerase (Promega, Madison, Wis.), and a final concentration of 50 mM Tris-HCl (pH 8.7), 40 mM KCl, 1 mM DTT, 0.5 mM of each dNTP, 4 mM MgCl$_2$, 0.12 μM Limiting primer, and 0.9 μM Excess primer was prepared. A 25-cycle amplification was run at 95° C. for 20 sec, 60° C. for 30 sec, and 72° C. for 45 sec, using the AG 9600 Cycler (Biotronics). This PCR product mixture was then subjected to semi-nested amplification and detection. HAV (Hepatitis A Virus): Extracted HAV RNA was first reverse transcribed. The reverse transcription was carried out in 20 μL sample volumes with 50 mM Tris-HCl (pH 8.9), 75 mM KCl, 10 mM DTT, 1.5 mM MgCl$_2$, 0.2 mM of each dNTP, 0.12 μM reverse primer, 12U RNASE Inhibitor, RNasin (Promega Corp, Madison, Wis.) and 20U M-MLV reverse transcriptase (Gibco). The reaction was carried out at 42° C. for 45 min, 90° C. for 2 min, and 25° C. for 20 sec, using the AG 9600 Cycler (Biotronics). After reverse transcription, these samples were amplified by PCR.

The reverse transcribed HAV RNA, now a DNA transcript, was then subjected to PCR amplification according to the following protocol. A 24 μL sample containing IU of Taq polymerase (Promega), and a final concentration of 50 mM Tris-HCl (pH 8.7), 40 mM KCl, 1 mM DTT, 0.5 mM of each dNTP, 4 mM MgCl$_2$, 0.9 μM forward primer and 0.9 μM of reverse primer was prepared. A 35-cycle amplification was run at 94° C. for 30 sec, 50° C. for 30 sec, and 72° C. for 90 sec. After PCR was complete, 10 μL of the PCR product was run on a 5% polyacrylamide gel, stained with ethidium bromide, and visualized under UV light, and the electrophoretogram is shown in FIG. 1. The following HAV primers used:

Forward Primer: 5' GCCGTTTGCCTAGGCTATAG3' (SEQ ID NO:1)
Reverse Primer: 5' CTCCTACAGCTCCATGCTA3' (SEQ ID NO:2)

The results for the nucleic acids that were subjected to quantitative PCR analysis are shown in Table 2.

TABLE 2

| | Dilution | Virus Quantity (log (molecules/mL)) | | |
| --- | --- | --- | --- | --- |
| | ($10^X$) | Prior Art | Invention | Ratio[6] |
| HCV RNA[1] | −1 | 6.55 | 6.60 | 1.12 |
| | −2 | 5.73 | 5.75 | 1.05 |
| | −3 | 4.81 | 4.97 | 1.45 |
| | −4 | 3.71 | 3.64 | 0.85 |
| HIV RNA[2] | 0 | 7.79 | 7.72 | 0.85 |
| | −1 | 7.00 | 6.88 | 0.76 |
| | −2 | 5.90 | 5.74 | 0.69 |
| | −3 | 5.10 | 4.90 | 0.63 |
| HIV DNA[3] | 0 | 7.82 | 7.77 | 0.89 |
| | −1 | 7.95 | 6.69 | 0.055 |
| | −2 | 6.59 | 5.55 | 0.091 |
| HBV DNA[4] | −1 | 5.34 | 3.67 | 0.021 |
| | −2 | 3.70 | 3.21 | 0.32 |
| HAV RNA[5] | See Figure 1 | | | |

[1]HCV RNA was purified from human blood plasma as described.
[2]HIV RNA was purified from the cell supernatant of centrifuged HIV infected PBL cells.
[3]HIV DNA was purified from normal human serum to which a 2 KB plasmid containing HIV-I was added.
[4]HBV DNA was purified from the serum of a chimpanzee infected with HBV.
[5]HAV RNA was purified from the supernatant of centrifuged BSCL cells infected with HAV.

TABLE 2-continued

| Dilution | Virus Quantity (log (molecules/mL)) | | |
| --- | --- | --- | --- |
| ($10^X$) | Prior Art | Invention | Ratio[6] |

[6]Ratio = the number of molecules of virus obtained using the method of the invention divided by the number of molecules of virus obtained using the prior art method.

These results demonstrate that the method of the invention enables the purification of HCV RNA and HIV RNA. Moreover, the differences in efficiency of recovery of HCV RNA and HIV RNA between the method of the invention and the prior art method are statistically insignificant. This is also shown by the ratio of molecules of RNA obtained using the method of the invention to the molecules of RNA obtained using the prior art method. For example, where the purification was carried out from HCV-positive human blood serum, it can be seen from Table 2 that there were no appreciable differences between the two methods.

This example also shows that the method of the invention quantitatively purifies RNA. This was demonstrated by the results obtained with HCV RNA where 10-fold differences in recovery were found to directly correlate with 10-fold dilutions of the sample. FIG. 1 shows a 5% polyacrylamide gel that compares the prior art system with the method of the invention for the purification of the HAV-containing sample. This figure visually demonstrates that the method of the invention and the prior art system provide very similar results.

Both FIG. 1 and Table 2 demonstrate that the method of the invention was at least as effective as the prior art method for RNA purification.

Comparing the efficiency of DNA recovery for the purification of the DNA samples of HIV DNA and HBV DNA using the two methods, it is clear from the results presented in Table 2 that the prior art system cannot distinguish between RNA and DNA. By contrast, the method of the invention does show different binding efficiencies for RNA and DNA. That the hydrophilic PVDF of the invention was found to be highly specific for RNA was an unexpected result. The commonly used silica gel nucleic acid binding medium cannot distinguish between nucleic acids (QIAGEN News 1995).

The unusual capacity of the method of the invention to discriminate between RNA and DNA makes possible its adaptation to the purification of RNA from samples that contain mixtures of RNA and DNA. This can be useful in cases in which a biological sample contains contaminating DNA, and purified RNA is needed. Repeated purification cycles using the method of the invention would prepare a sample of substantially purified RNA. Each cycle would concentrate the RNA relative to the DNA present in the sample. A series of iterations would eventually achieve a substantially purified RNA sample.

EXAMPLE 3

RNA Percentage Recovery Comparison

This example further demonstrates the effectiveness of the method the invention for purifying viral RNA. In this example synthetic hepatitis C virus H strain (HCV-H) RNA was used. Full length HCV-H (Accession No. M67463, Inchauspe et al. 1991) was cloned into a pBluescript-SK vector (Stratagene, La Jolla, Calif.) which contains a T7 promoter upstream of the 5' UTR (Inchauspe et al. 1991). Synthetic HCV RNA was labeled with $^3$H during in vitro transcription, where transcripts were synthesized from the linearized cDNA template following a standard protocol (Schenborn et al. 1985). The MEGAscript T7 polymerase kit was used (Ambion, Austin, Tex.). For labeling, UTP/$^3$H-UTP was mixed at a 17:1 ratio.

The synthetic RNA samples were subjected to nucleic acid purification. Synthetic $^3$H-RNA (50 µL) was added to 560 µL of lysis solution (5 M GuSCN, 40 mM Tris-HCl, 20 mM EDTA, and 1% Triton X-100). The samples were vortexed, incubated for 10 min, and then 560 µL of ethanol was added to each sample. These samples were then applied to the filters of 96-well MultiScreen®-GV filtration plates (Millipore) containing 0.22 µm hydrophilic PVDF membranes defining the bottoms of the wells. A vacuum was used to draw the sample solution through the filters.

The samples were then washed twice with 300 µL of washing solution (75 MM NaCl, 10 mM Tris-HCl, 2 mM EDTA, in 50% ethanol). The bound RNA was then eluted with 50 µL of a hot (80° C.) eluting solution (nuclease-free 10 mM Tris-HCl, 1 mM EDTA). For comparison, samples of the synthetic $^3$H-RNA were treated in this same way and processed by the prior art nucleic purification method.

RNA % recovery, when samples of different quantities of HCV RNA were applied to and eluted from either hydrophilic PVDF or the prior art system, was determined by measuring $^3$H counts.

A solution of 4 ng/µL (8×10$^8$ mols/µL) of $^3$H-RNA was diluted in series. Samples (50 µL) of these dilutions were then subjected to purification by the method of the invention or by the prior art system following the same procedures as those used for viral nucleic acid purification. The counts from the purified samples were compared to the counts from 50 µL of untreated $^3$H-RNA to determine the percent recovery using the two different systems.

To measure counts, samples of 50 µL were mixed with 200 µL Optiphase SuperMix (Wallac, Milton Keynes, UK) and read on a 1450 Microbeta Plus (Wallac, Gaithersburg, Md.) liquid scintillation counter.

The results are shown in Table 3.

TABLE 3

Comparison of RNA % Recovery at Different Amounts

| RNA ng (molecules) | n | Prior Art (%) | Invention (%) |
|---|---|---|---|
| 0.4 ng (8 × 10$^7$) | 6/6 | 51.67 ± 10.84 | 60.17 ± 29.42 |
| 4 ng (8 × 10$^8$) | 6/5 | 75.00 ± 16.71 | 75.60 ± 13.90 |
| 40 ng (8 × 10$^9$) | 6/6 | 86.00 ± 11.52 | 70.17 ± 6.49 |
| Average | 18/17 | 70 ± 19.31 | 68.24 ± 19.36 |

RNA % recovery was determined by dividing the counts obtained from the RNA that had gone through the RNA purification methodology by the counts of RNA measured from an RNA standard sample.
n is the number of samples used for both the prior art system and the method of the invention (prior art/invention).
t test comparison of the methods: t test = 0.6875

Table 3 illustrates the comparative recovery efficiency of the method of the invention and the prior art method. The results in Table 3 demonstrate that there was no statistical difference between the RNA % recovery using the hydrophilic PVDF filter method of the invention and the prior art method. These results confirm those obtained by quantitative PCR as shown in Example 2 (see Table 2). The unexpected efficacy of hydrophilic PVDF for RNA binding has been further demonstrated by these results.

The results in Table 3 also demonstrate that the RNA binding efficiency using the method of the invention was about 70%, which is much greater than the DNA binding found in Example 2.

EXAMPLE 4
Comparison of Different Filter Types and Pore Sizes

This example demonstrates the effect of pore size and membrane type on viral RNA membrane binding. Samples were prepared as described in Example 3, and were applied to the different filters. The results are shown in Table 4.

TABLE 4A

Comparison of Hydrophilic PVDF Filter Pore Sizes on RNA % Recovery

| Filter Pore Size | 0.22 µm | 0.45 µm | 0.65 µm |
|---|---|---|---|
| RNA % Recovery | 41 ± 10% | 8 ± 6% | 4 ± 3% |

(Average of 6 samples ± SD)

TABLE 4B

Comparison of Filter Types on RNA % Recovery

| Filter Type | IP[1] | NP[2] | GV[3] | DE[4] |
|---|---|---|---|---|
| RNA % Recovery | NA* | 12 ± 3% | 38 ± 8% | 3 ± 0.8% |

(Average of 4 samples ± SD)
*Due to blockage on the filter, samples could not be recovered.
Filter types:
[1]IP is 0.45 µm Immobilon-p hydrophobic PVDF, high protein/nucleic acid binding.
[2]NP is 0.2 µm, Immobilon-NC nitrocellulose, high protein/nucleic acid binding.
[3]GV is 0.22 µm, Durapore ® hydrophilic PVDF, low protein/nucleic acid binding.
[4]DE is 0.65 µm, Positively charged DEAE (diethylaminoethyl).
The µm values represent the pore size of the different filters.

Table 4A shows that the 0.22 µm pore size membrane was the most efficient membrane of those tested for purifying RNA. Table 4B demonstrates that for RNA purification, the 0.22 µm hydrophilic, low protein-binding PVDF membrane was the most effective one tested. It is believed that the lower RNA % recovery found in this example as compared to the results in Example 3 is due to the breakdown of the labeled RNA molecules. Some of the $^3$H had come off of the RNA molecule over time, causing a lower calculated % RNA bound.

EXAMPLE 5
Screening Blood for Viruses

The method of the invention is highly useful for screening blood for viruses. Samples of blood are collected, and cellular components are then removed to produce a cell-free sample, e.g., serum or plasma. This step can be accomplished by centrifugation. The cell-free sample is then lysed using an appropriate lysis solution. The lysed sample is applied to a hydrophilic PVDF membrane containing pores having an average diameter of less than about 0.45 µm. The sample is then passed through the membrane to selectively retain the viral nucleic acid. The membrane is washed using a wash solution, and the viral nucleic acid is then eluted from the membrane using low salt eluting solution as previously described. A purified nucleic acid solution is then recovered. The viral nucleic acid is then identified using amplification technology, e.g., PCR (Clewley 1995).

The method of the invention is compatible with handling a multitude of samples simultaneously in an automatable way so that the identification of viruses present in many blood samples can achieved simultaneously.

EXAMPLE 6
Evaluating the Effectiveness of Antiviral Drugs and Vaccines

The method of the invention can be used to evaluate the effectiveness of antiviral drugs and vaccines. A mammal, e.g., human, chimpanzee or other primate, can be infected with a virus, or can be vaccinated and then challenged with virus.

To test the effectiveness of an antiviral drug a procedure such as the following can be carried out. First, the antiviral drug is administered to the infected animal. The blood is sampled at various times. The blood samples are centrifuged to remove the cellular components, to provide plasma. Then the plasma is treated with a lysis solution, and the resulting fluid is applied to the filters. The filters, with or without bound RNA, are then washed with wash solution, and the purified nucleic acid is eluted with eluting solution. Quantitative PCR is then performed to determine the extent of the viral infection. The method of the invention, therefore, is useful in the rapid assessment of an antiviral drug's effectiveness.

To test vaccines, a mammal is first vaccinated against the virus of interest. Then, after waiting an appropriate period of time, the mammal is challenged with virus. The blood is sampled at various times, and virus is extracted from the plasma or serum as previously described. The viral load is quantitated using nucleic acid amplification technologies as previously described. When these results are compared to those obtained with an animal that has not been administered the vaccine, the effectiveness of vaccines can be rapidly assessed.

EXAMPLE 7
Separation of RNA and DNA from Mixtures Contain Both

The method of the invention is used to substantially increase the proportion of RNA to DNA in a sample that contains a mixture of the two nucleic acids. Using the finding, see Table 2, that the hydrophilic PVDF filters of the method of the invention bind RNA with considerably more specificity than DNA, mixed solutions of nucleic acid that contain RNA and DNA are substantially enriched in RNA when this filter system is used to purify the RNA present.

Since the filters can be repetitively used, to substantially purify the RNA component relative to the DNA component of the mixture the samples should be reapplied to the membrane filters of the invention. Each iteration will purify the RNA relative to the DNA until a solution of substantially purified RNA is obtained.

EXAMPLE 8
Purification of Viral RNA from Lymphocytes

The method of the invention is also useful for purification of viral nucleic acid from lymphocytes. Viruses such as HIV are found in lymphocytes. It is important to have a rapid means for testing to what extent an HIV infection may have been eliminated from a person, therefore isolating viral RNA from lymphocytes would be a valuable use for the method of the invention. Since after the initial stages of HIV infection, most of the virus is present in the lymphocytes, this approach should be usefull for determining the level of infection over long periods of time.

Lymphocytes (white blood cells) are separated from blood by centrifugation using standard protocols. Whole blood, under nonclotting conditions and in the presence of heparin, is layered over HISTOPAQUE® (Sigma Chemical Company, St. Louis, Mo.). The sample is centrifuged at 400×g for 30 minutes at room temperature. The upper layer is removed and the lymphocytes are found in the opaque interface region. The opaque region containing the lymphocytes is then removed washed with buffer and then collected according to standard procedures (Sigma Diagnostics, HISTOPAQUE®-1077). Lymphocytes are then lysed using the lysis solution as previously described, except further having 1% mercaptoethanol, then homogenized and treated by the method of the invention. Purification of viral RNA according to the method of the invention makes possible the rapid detection of HIV present in lymphocytes.

Thus, while there have been described what are presently believed to be the preferred embodiments of the present invention, those skilled in the art will realize that other and further embodiments can be made without departing from the spirit of the invention, and it is intended to include all such further modifications and changes as come within the true scope of the claims set forth herein.

EXAMPLE 9
DNA Recovery when Silica Beads are added to a Biological Sample

This example demonstrates that the recovery of DNA using the method of the invention can be improved by adding silica beads to the biological sample prior to contacting the biological sample with the PVDF membrane.

HBV (Hepatitis B virus) DNA was extracted from human blood plasma. Blood plasma was prepared by centrifuging a sample of HBV-infected blood in the presence on anticoagulation agents. Samples of the HBV DNA were then taken and 20 µL of silica beads, which can be obtained from Bangs Laboratories (Carmel, Ind.) as Product No. 50004000PN, were added to each sample. Each sample was then subjected to the method of the invention. The results of this example are shown in Table 5 below.

TABLE 5

| | | HBV Recovery (log (molecules/mL)) | | |
|---|---|---|---|---|
| | Dilution ($10^x$) | Prior Art | Invention | Invention with Silica Beads[2] |
| HBV DNA[1] | −1 | 6.25 | 5.79 | 6.10 |
| | −2 | 5.24 | 4.35 | 5.05 |
| | −3 | 4.29 | 3.96 | 4.28 |

[1]HBV 75-564 was diluted in human negative serum.
[2]20 µl of silica beads (4 µm, 20% solid, Bangs Laboratories (Camel, Indiana)) was added to the sample prior to contacting the sample with the PVDF membrane.

Table 5 shows that HBV DNA purification can be enhanced by adding silica beads to the sample prior to contacting the sample with a PVDF membrane. The HBV DNA recovery without the addition of silica beads to the sample was 34–46% to that of the prior art Qiagen method. Adding silica beads to the sample prior to contacting the sample with the PVDF membrane improved HBV DNA recovery to 65–97% to that of the Qiagen method.

EXAMPLE 10
The Presence of Silica Beads Interfering with RNA recovery

This example demonstrates that RNA recovery is not affected by the addition of silica beads to a biological sample prior to contacting the biological sample with the PVDF membrane.

Blood from an HCV-infected patient was centrifuged and human blood serum was removed. RNA was then extracted from the human blood serum. 20 ul of silica beads (from Bangs Laboratories (Carmel, Ind.)) were then added to the samples of HCV RNA. Samples of the HCV RNA were then brought into contact with a PVDF membrane in accordance with the present invention. The samples were then passed through the PVDF membrane by vacuum filtration and then washed with a wash solution as described in Example 1. The RNA bound on the PVDF membrane was then eluted as previously discussed in Example 1. The samples were then collected in this elution step and purified RNA was then subjected to further analysis. In particular, quantitative PCR was done using the AmpliSensor® assay system (Biotronics). The results of this example are shown below in Table 6.

TABLE 6

| | | HCV Recovery (log (molecules/mL)) | |
|---|---|---|---|
| | Dilution (10$^x$) | Prior Art | Invention | Invention with Silica Beads[2] |
| HCV DNA[1] | −1 | 7.42 | 7.30 | 7.29 |
| | −2 | 6.43 | 6.25 | 6.12 |
| | −3 | 5.38 | 5.27 | 5.20 |

[1]HCV RNA was extracted from human blood serum.
[2]20 μl of silica beads (4 μm, 20% solid, Bangs Laboratories (Carmel, Indiana)) was added to the sample before the sample was brought into contact with the PVDF membrane.

Table 6 shows the recovery of HCV RNA using the prior art Qiagen method, the method of the invention and the method of the invention in the presence of silica beads. As is readily apparent from the data, HCV RNA recovery was not affected by the addition of silica beads in the samples prior to contacting the samples with the PVDF membrane.

EXAMPLE 11
Feasibility of Automatic Procedures with the Invention

This example demonstrates that automated sample preparation with the invention is feasible and equivalent to preparation with the prior art Qiagen method.

A sample of blood was taken from an HCV infected patient. The sample of blood was centrifuged in the presence of anti-coagulation agents and blood serum was removed. RNA was then extracted from the blood serum. HCV RNA samples were then subjected to lysis.

In particular, 500 μL of a lysis solution (5M GuSCN, 40 mM Tris-HCl, 20mM EDTA and 1% Triton X-100) was delivered to a 96-well microtiter plate using a wash tool on the Biomek 2000 (Beckman Instruments). The wash tool delivers or osperates the bulk amount of the liquid. The microtiter plate has a capacity of 2 ml and is manufactured by Marsh Corporation (Rochester, N.Y.). 140 μL of the HCV RNA samples were then added to the microtiter plate. Using the pipette mix finction which draws and dispenses through pipette tips, the samples were mixed with the lysis solution 10 times using the pipette tool. Then, 500 μL of ethanol was delivered to the microtiter plate using the wash tool on the Biomek 2000 (Beckman Instruments). The samples and ethanol were mixed ten times using the pipette tool.

Then, 300 μL of the samples were transferred using a pipette tool to a PVDF filter plate furnished by Millipore Corporation (Bedford, Mass.). The samples were then passed through the filter by vacuum filtration. The use of vacuum filtration in this experiment demonstrates the invention's adaptability to automation using laboratory robotics. Robotics enables the user of the method to simultaneously deliver all of the samples to the wells of the filter plate such that a plurality of samples can be handled at one time. Laboratory robotics is now in common use in laboratories.

Vacuum filtration was repeated with an additional 300 μl of the lysis solution The PVDF filter plate was then washed three times by vacuum filtration using 300 μL of wash solution (75 mM NaCl, 10 mM Tris-HCl, 2mM EDTA in 50% ethanol). The PVDF filter plate was then dried under a vacuum for 10 minutes and then dried for an additional 10 minutes without a vacuum. The bound RNA was then eluted with 50 μL of a hot (80° C.), nuclease free H$_2$O. The samples were collected in this elution step in a 96-well microtiter plate. The purified RNA was then subjected to further analysis.

Quantitative PCR assays were done using the AmpliSensor® assay system (Biotronics). The results are shown in Table 7.

TABLE 7

| | | RNA Recovery (log (molecules/mL)) | |
|---|---|---|---|
| | Dilution (10$^x$) | Prior Art | Invention |
| HBV DNA[1] | −2 | 6.32 | 6.13 |
| | −3 | 5.13 | 5.12 |
| | −4 | 4.24 | 4.10 |

Table 7 shows that robotic automated sample preparation is feasible. As apparent from the data in Table 7, there was very little difference in RNA recovery between the prior art Qiagen method and the robotic automated method of the invention. Accordingly, the robotic automated method of the invention has equivalent sensitivity to that of the Qiagen method.

EXAMPLE 12
RNA Recovery with the Invention

This example compares the robotic automated method of this invention to the Qiagen method of RNA recovery.

Blood was taken from several HCV-infected chimpanzees and then centrifuged. Samples of serum were then taken from the blood and RNA was extracted from the serum samples. Each RNA sample was then subjected to the robotic automated method of this invention and the Qiagen method. Purified RNA was recovered by both methods and then quantitative PCR was performed on each sample using the AmpliSensor® assay system (Biotronics). The results of this example are shown below in Table 8.

TABLE 8

| | | RNA Recovery (log (molecules/mL)) | |
|---|---|---|---|
| | Sample | Prior Art | Invention |
| HCV RNA | 1 | 5.67 | 6.00 |
| | 2 | 6.48 | 6.58 |
| | 3 | 8.08 | 8.02 |
| | 4 | 7.45 | 7.36 |
| | 5 | 6.98 | 6.72 |
| | 6 | 5.00 | 5.47 |
| | 7 | 7.54 | 7.08 |
| | 8 | 6.53 | 6.73 |
| | 9 | 7.86 | 7.01 |
| | 10 | 7.13 | 7.08 |
| | 11 | 6.94 | 7.01 |
| | Mean | 6.88 | 6.82 |

Although there were slight variations in the quantities recovered by the two methods, the mean of the data showed very little difference in recovery of RNA. Accordingly, the robotic automated method of this invention can replace the Qiagen method for recovery of RNA.

BIBLIOGRAPHY

The following publications, mentioned in the foregoing specification, are incorporated herein by reference for all that they disclose:

Ali N and Jameel S, "Direct detection of hepatitis C virus RNA in serum by reverse transcription PCR," *BioTechniques* 15:40 (1993).

Cheung R C, Matsui S M, and Greenberg H B, "Rapid and sensitive method for detection of hepatitis C virus RNA by using silica particles," *J Clin Microbiol* 32:2593–2597 (1994).

Chomczynski P and Sacchi N, "Single-Step Method of RNA Isolation by Acid Guanidinium Thiocyanate-Phenol-Chloroform Extraction." *Anal Biochem* 162:156–159 (1987).

Clewley J P, ed., *The Polymerase Chain Reaction (PCR) for Human Viral Diagnosis*, CRC Press, Boca Raton, Fla., Chapter 5 (1995).

Dieffenbach C W and Dveksler G S, eds., *PCR Primer: A Laboratory Manual*, Cold Spring Harbor Laboratory Press, New York (1995).

Gretch D, Lee W, and Corey L, "Use of aminotransferase, hepatitis C antibody, and hepatitis C polymerase chain reaction RNA assays to establish the diagnosis of hepatitis C virus infection in a diagnostic virology laboratory," *J Clin Microbiol* 30:2145–2149 (1992).

Hames B D and Higgins S J, eds., *Gene Probes I and Gene Probes II*, IRL Press, Oxford (1995).

Hayashi Y, Kaneko S, Jomori T, Kobara Y, Suzuki E, Tasaka F, Murakami S, Kobayashi K, and Mitani T, "A simple single-tube procedure of PCR assay for the detection of hepatitis C virus RNA," *Res Virol* 145:123–128 (1994).

Inchauspe G, Zebedee S L, Lee D-HH, Sugitani M, Nasoff M S, and Prince A M, "Genomic structure of the human prototype strain H of hepatitis C virus: Comparison with American and Japanese Isolates," *Proc Natl Acad Sci USA* 88:10292–10296 (1991).

Kaneko S, Feinstone S M, and Miller R H "Rapid and sensitive method for the detection of serum hepatitis B virus DNA using the Polymerase Chain Reaction technique," *Clin Microbiol* 27: 1930–1933 (1989).

Keller G H and Manak M M, *DNA Probes*, 2d ed., Macmillan Publishers Ltd., England (1991).

Lai J, Prince A M, Wolf L, and Andrus L, "A simplified method for PCR detection of hepatitis C virus RNA from human serum," *PCR Methods Appl* 3:9308–9309 (1994).

QIAGEN News (1995).

QIAGEN Catalogue (1997).

Ravaggi A, Primi D, and Cariani E, "Direct PCR amplification of HCV RNA from human serum," *PCR Methods Appl* 1:291–292 (1992).

Sambrook J, Fritsch E F, and Maniatis T, *Molecular Cloning. A Laboratory Manual*, 2d ed., Cold Spring Harbor Laboratory, Cold Spring Harbor (1989).

Schenborn E T and Mierindorf R C "A Novel transcription property of SP6 and T7 RNA polymerases: Dependence on template structure" *Nucl Acids Res* 13:6223–6236 (1985).

Wang C N, Wu K Y, and Wang H T, "Quantitative PCR using the AmpliSensor Assay," in Dieffenbach C W and Dveksler G S, eds., *PCR Primer: A Laboratory Manual*, Cold Spring Harbor Laboratory Press, Cold Spring Harbor, N.Y., pp. 193–202 (1995).

What is claimed is:

1. A method for purifying a nucleic acid, comprising:
  (a) contacting a biological sample containing a nucleic acid with a hydrophilic polyvinylidine fluoride (PVDF) membrane which contains pores having an average diameter less than about 0.45 µm; and
  (b) recovering the nucleic acid.

2. A method according to claim 1, further comprising adding silica beads to the biological sample prior to the contacting step.

3. A method according to claim 2, wherein the silica beads have an average diameter of from about 0.2 microns to about 5.0 microns.

4. A method according to claim 1, wherein said nucleic acid is RNA.

5. A method according to claim 4, wherein said RNA is viral RNA.

6. A method according to claim 1, wherein said nucleic acid is DNA.

7. A method according to claim 1, wherein the membrane contains pores having an average diameter of from about 0.1 µm to about 0.3 µm.

8. A method according to claim 7, wherein the membrane contains pores having an average diameter of from about 0.15 µm to about 0.25 µm.

9. A method according to claim 8, wherein the membrane contains pores having an average diameter of about 0.22 µm.

10. A method according to claim 1, wherein the hydrophilic PVDF membrane is low protein-binding.

11. A method according to claim 1, further comprising applying a pressure differential across the membrane after the contacting step.

12. A method according to claim 11, wherein the applying step comprises applying negative pressure below the membrane.

13. A method according to claim 11, wherein the applying step comprises applying positive pressure above the membrane.

14. A method according to claim 1, wherein the contacting step comprises applying centrifugal force.

15. A method according to claim 1, further comprising lysing the biological sample before the contacting step.

16. A method according to claim 15, further comprising adding silica beads to the biological sample after the lysing step and prior to the contacting step.

17. A method according to claim 1, wherein the nucleic acid has a length less than about 40,000 nucleotides.

18. A method according to claim 1, wherein the nucleic acid has a length less than about 30,000 nucleotides.

19. A method according to claim 1, further comprising removing cellular components of the biological sample prior to contacting the biological sample to the membrane.

20. A method according to claim 19, wherein the biological sample is a blood sample, and blood cells are removed from the biological sample after the contacting step and prior to the recovering step.

21. A method according to claim 19, wherein the biological sample is a cell culture, and the cultured cells are removed from the culture medium after the contacting step and prior to the recovering step.

22. A method according to claim 1, wherein the biological sample is substantially free of cellular components.

23. A method according to claim 22, wherein the biological sample is serum or plasma.

24. A method according to claim 1, further comprising amplifying the nucleic acid to provide an amplified nucleic acid.

25. A method according to claim 24, further comprising quantitating the amplified nucleic acid.

26. A method according to claim 25, wherein the quantitating comprises amplifying the nucleic acid using RT-PCR.

27. A method according to claim 1, further comprising identifying the nucleic acid by hybridizing with an oligonucleotide probe that uniquely hybridizes with the nucleic acid.

* * * * *

UNITED STATES PATENT AND TRADEMARK OFFICE
CERTIFICATE OF CORRECTION

PATENT NO. : 6,274,308 B1
DATED : August 14, 2001
INVENTOR(S) : Lee et al.

It is certified that error appears in the above-identified patent and that said Letters Patent is hereby corrected as shown below:

Column 17,
Line 25, now reads "containing IU" should read -- containing 1U --;

Column 18,
Line 65, now reads "in vitro" should read -- in *vitro* --;

Column 19,
Line 16, now reads "(75 MM NaCl" should read -- (75mM NaCl --;

Column 22,
Line 36, now reads "4.35" should read -- 4.85 --;

Signed and Sealed this

Ninth Day of July, 2002

Attest:

*Attesting Officer*

JAMES E. ROGAN
*Director of the United States Patent and Trademark Office*